US00PP27434P2

(12) United States Plant Patent
MacKenzie

(10) Patent No.: US PP27,434 P2
(45) Date of Patent: Nov. 29, 2016

(54) ***LIRIOPE* PLANT NAMED 'NONGMN'**

(50) Latin Name: *Liriope minor*
Varietal Denomination: Nongmn

(71) Applicant: David MacKenzie, Nunica, MI (US)

(72) Inventor: David MacKenzie, Nunica, MI (US)

(73) Assignee: HORTECH, INC., Spring Lake, MI (US)

( * ) Notice: Subject to any disclaimer, the term of this patent is extended or adjusted under 35 U.S.C. 154(b) by 178 days.

(21) Appl. No.: 14/121,532

(22) Filed: Sep. 16, 2014

(51) Int. Cl.
*A01H 5/00* (2006.01)

(52) U.S. Cl.
USPC ..... Plt./450

(58) Field of Classification Search
USPC ..... Plt./450
See application file for complete search history.

*Primary Examiner* — Keith Robinson
(74) *Attorney, Agent, or Firm* — Penny J. Aguirre

(57) ABSTRACT

A new cultivar of *Liriope* minor called 'Nongmn', that is characterized by its foliage that reaches a height of only 10 cm, its flower stems that reach a height of only 7 cm and its dense, low growing plant habit that forms a turf-like thicket.

2 Drawing Sheets

Botanical classification: *Lirope minor.*
Variety denomination: 'Nongmn'.

BACKGROUND OF THE INVENTION

The present invention relates to a new and distinct cultivar of *Liriope minor* named 'Nongmn' and will be referred to hereafter by its cultivar name, 'Nongmn'. The new cultivar represents a new herbaceous perennial grown for landscape use.

The new cultivar was developed by the Inventor at his nursery in Nunica, Mich. Approximately 10,000 seeds, resulting from the open pollination of a proprietary unnamed *Liriope minor* plant (not patented) in the Inventor's breeding program, were sown. 'Nongmn' was selected in June 2004 from amongst the resulting seedlings Asexual propagation of the new cultivar was first accomplished by division in Nunica, Mich. in June of 2005 by the Inventor. Asexual propagation by division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Nongmn' as a unique cultivar of *Liriope*.

1. 'Nongmn' exhibits foliage that reaches a height of only 10 cm.
2. 'Nongmn' exhibits flower stems that reach a height of only 7 cm.
3. 'Nongmn' exhibits a dense, low growing plant habit that forms a turf-like thicket.

Typical plants of *Liriope minor*, the parent species of 'Nongmn', differ from 'Nongmn' in having foliage that reaches 20 cm in height and flower stems that reach 10 cm in length. All other attributes are similar. 'Nongmn' can be compared to *Liriope minor* cultivar 'Torafu' (not patented). 'Torafu' is similar to 'Nongmn' in foliage height, but differs from 'Nongmn' in having foliage with irregular creamy yellow horizontal bands and in having a less dense growth habit. There are no other cultivars of *Liriope minor* known to the Inventor.

BRIEF DESCRIPTION OF THE DRAWINGS

The accompanying colored photographs illustrate the overall appearance and distinct characteristics of the new *Liriope*. The photographs were taken of 1-year-old plants as grown in the ground in Nunica, Mich.

The photograph in FIG. 1 provides a view of a mass planting of 'Nongmn' in bloom.

Figure 1:
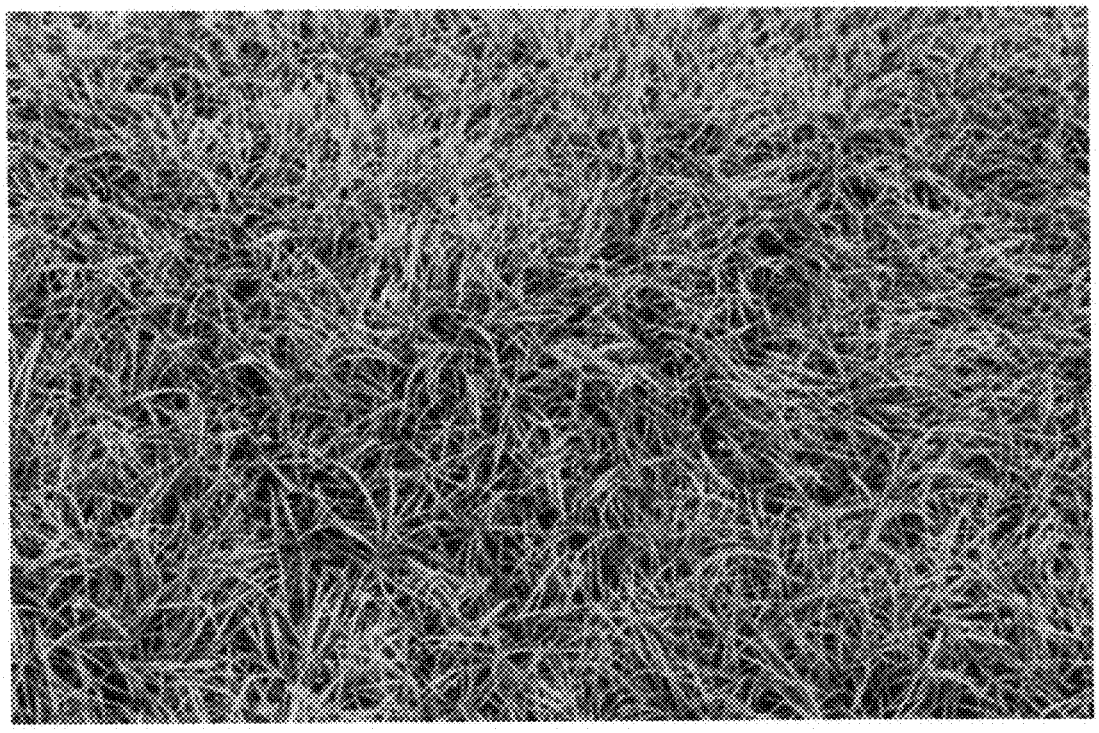
Figure 2:
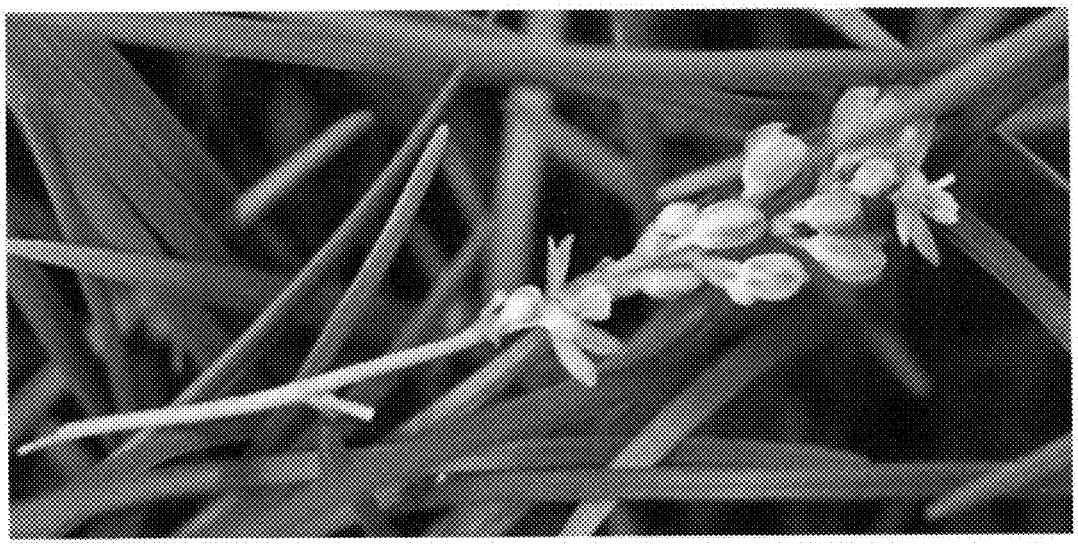

The photograph in FIG. 2 provides a view of an inflorescence of 'Nongmn'.

Figure 3:
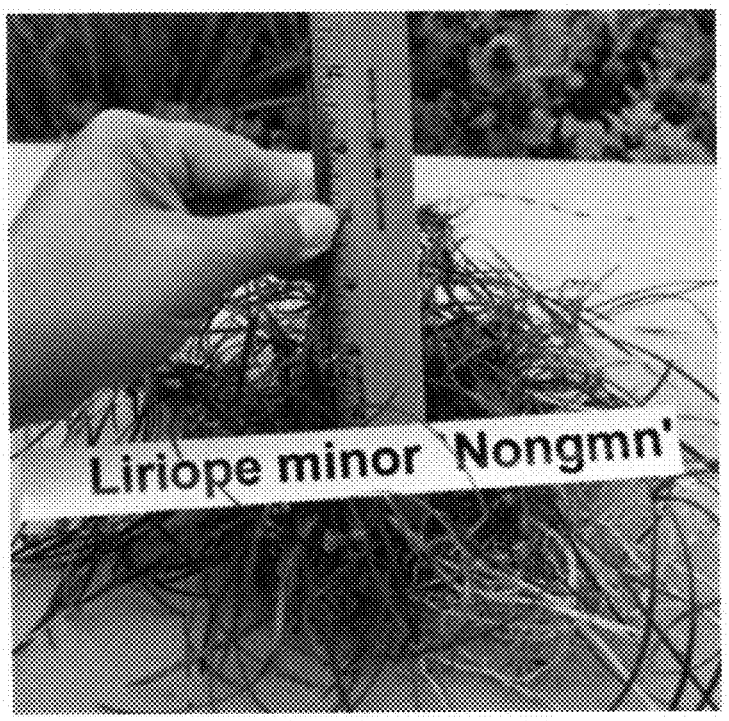

The photograph in FIG. 3 provides a view of the foliage height of 'Nongmn'.

The colors in the photographs may differ slightly from the color values cited in the detailed botanical description, which accurately describe the colors of the new *Liriope*.

DETAILED BOTANICAL DESCRIPTION

The following is a detailed description of three year-old plants of the new cultivar as grown outdoors in the Inventor's nursery in Nunica, Mich. The phenotype of the new cultivar may vary with variations in environmental, climatic, and cultural conditions, as it has not been tested under all possible environmental conditions. The color determination is in accordance with The 1988 R.H.S. Colour Chart of The Royal Horticultural Society, London, England, except where general color terms of ordinary dictionary significance are used.

General description:

*Blooming period.*—About 4 weeks starting in late August in Nunica, Mich.

*Plant habit.*—Herbaceous thicket forming turf-like perennial, with low growing habit, mature plants spread by underground rhizomes, no above ground stems.

*Height and spread.*—Mature plants reach about 10 cm in height and 1 m in width.

*Cold hardiness.*—At least to U.S.D.A. Zone 4.

*Diseases and pests.*—No susceptibility or resistance to diseases or pests has been observed.

*Root description.*—Fibrous on creeping rootstocks that are an average of 20 cm in length and 1 mm in width, 158C in color.

*Growth rate.*—Relatively slow, approximately 20 cm per year.

*Propagation.*—Division.

*Time required for root development.*—An average of four weeks for root initiation with a rooted young plant produced after an average of eight weeks.

Foliage description:

*Leaf shape.*—Lanceolate-linear.

*Leaf division.*—Simple.

*Leaf base.*—Truncate.

*Leaf apex.*—Acute.

*Leaf venation.*—Parallel, 5 to 7 nerved, 145A in color on upper surface, 138B in color on lower surface.

*Leaf margins.*—Entire.

*Leaf attachment.*—Sessile to rhizome.

*Leaf arrangement.*—Whorled and surrounding the crown and arising at the tips of the spreading rhizomes.

*Leaf surface.*—Smooth on both surfaces.

*Leaf color.*—Young and mature leaves upper surface 137B, young and mature leaves lower surface 138B.

*Leaf size.*—Up to 15 cm in length and 2 to 3 mm in width.

*Leaf aspect.*—Arching.

*Leaf quantity.*—Average of 8 per crown.

Flower description:

*Inflorescence type.*—Racemes.

*Inflorescence size.*—About 3 cm in length and 1 cm in width.

*Lastingness of inflorescence.*—About 4 weeks from first flower to last flower.

*Flower size.*—Average of 1 cm in width and 0.5 in depth.

*Flower fragrance.*—None.

*Flower number.*—7 to 11 per scape.

*Flower aspect.*—Flowers upright to outward.

*Flower bud.*—5 to 6 mm (including calyx) in length and an average of 4 mm in width, oblong in shape, color of petal portion 92A suffused with 92C near apex, color of base 92C.

*Flower form.*—Campanulate.

*Tepals.*—6, about 6 mm in length and 2 to 3 mm in width, upper one-third portion un-fused and obovate in shape, apex obtuse, base fused, margin entire, upper and lower surface glabrous, color; 92B on upper surface and 92A on lower surface.

*Pedicel.*—Elliptical in cross section shape; 1 mm×0.5 mm in width, 3 mm in length, glabrous surface, 138B in color, medium strength.

*Scape* (*peduncle*).—5 to 7 cm in length, elliptical in cross section; 1 mm×0.5 mm in width, 138B in color, glabrous surface, medium strength.

Reproductive organs:

*Gynoecium.*—1 pistil, average of 1.5 mm in length, stigma is 3-locular, 0.5 mm in length and width, rounded apex and 69C in color, style is an average of 1 mm in length and 0.6 mm in width, 69C in color, ovary is approximately 3 mm in diameter and 69C in color.

*Androcoecium.*—6 stamens, anthers are oblong with obtuse apex, an average of 0.8 mm in width and 1.2 mm in length, 14B in color, filaments are an average of 1.2 mm in length and 0.5 mm in width and 78B in color, pollen is low in quantity and 14B in color.

*Fruit.*—Globose in shape, 2 to 3 mm in diameter, 136A in color and maturing to N186A, smooth surface.

*Seed.*—Globose in shape, an average of 2.5 mm in diameter, 136B in color, smooth and shiny surface.

It is claimed:

1. A new and distinct cultivar of *Liriope* plant named 'Nongmn' as herein illustrated and described.

* * * * *